United States Patent [19]

Olsen

[11] 4,243,047

[45] Jan. 6, 1981

[54] INSTRUMENT FOR TAKING TISSUE SPECIMENS

[75] Inventor: C. Eric Olsen, Ventura, Calif.

[73] Assignee: Auburn Enterprises, Inc., Ventura, Calif.

[21] Appl. No.: 10,174

[22] Filed: Feb. 7, 1979

[51] Int. Cl.³ ............................................. A61B 10/00
[52] U.S. Cl. ...................................... 128/751; 30/128
[58] Field of Search ............................. 128/751–755; 30/128, 130, 174

[56] References Cited

U.S. PATENT DOCUMENTS

| 2,742,696 | 4/1956 | Williams | 30/128 |
|---|---|---|---|
| 3,353,531 | 11/1967 | Armao | 128/751 |
| 3,404,677 | 8/1968 | Springer | 128/751 |
| 3,585,985 | 6/1971 | Gould | 128/751 |
| 3,895,636 | 7/1975 | Schmidt | 128/305 |
| 4,043,343 | 8/1977 | Williams | 128/305 X |

Primary Examiner—Kyle L. Howell
Attorney, Agent, or Firm—Jack C. Munro

[57] ABSTRACT

In combination with an instrument for taking tissue specimens which comprises a pair of movable jaws. One jaw is capable of being located within a cavity of the other jaw. The tissue specimen is to be located within the cavity. Also located within the cavity is a biasing means in the form of a leaf spring which is to exert a continuous bias upon the tissue specimen and, upon opening of the jaws, the tissue specimen is automatically moved to the upper end of the cavity to facilitate its removal therefrom.

5 Claims, 4 Drawing Figures

INSTRUMENT FOR TAKING TISSUE SPECIMENS

BACKGROUND OF THE INVENTION

The field of this invention relates to medical instruments and more specifically to a surgical instrument to facilitate the taking of tissue specimens.

Medical practioners as a regular practice extract tissue sections by an instrument inserted into the body through a natural opening to remove tissue from an inaccessible region of the body. Specifically, the use of such a biopsy instrument is quite common within the vagina to remove tissue from the female uterine cervix. A common form of such an instrument employs a pair of movable jaws with the edge of one jaw including a cutting edge and that same jaw including a cavity. The first jaw is to be movable into the cavity in a close fitting arrangement. Therefore, with a piece of tissue located between the jaws and the jaws moved together, that tissue will be cut and removed.

With the tissue having been removed, the medical practioner removes the instrument and opens the jaws. The tissue section is usually quite samll with also the cavity of the instrument being quite small. The medical practioner must then remove the section of tissue from the cavity. The removal procedure for removing the tissue is by employing a toothpick or an equivalent device to "dig" the tissue out of the cavity.

Having to remove the tissue in this manner from the cavity frequently causes the tissue to come out in different sections and also causes undersirable tissue damage. In the performing of the biopsy, it is preferable that the tissue is as undamaged as possible so that the tissue is represented to be in its original state for the subsequent pathological examination.

Previously, there have been various types of instruments for taking tissue specimens. Essentially, each of the instruments of the prior art employ the use of a pair of jaws and by the closing of these jaws a tissue specimen is removed and is thereby located within a cavity of the instrument. Upon the instrument being removed from the inaccessible area, the jaws are then opened and the tissue sepcimen removed. Because the heads of these instruments are very small and likewise the cavity being very small, the tissue specimen is very small and cannot be very easily grasped. Therefore the medical practitioner has to "dig" the tissue out from the cavity usually by a toothpick, tweezers or other similar instrument.

Prior to this invention there was no known instrument which facilitated the removal of the tissue specimen upon the jaws of the instrument being open so that the tissue specimen was automatically removed from the cavity.

SUMMARY OF THE INVENTION

The structure of this invention is in relation to an existing tissue taking instrument of any type which employs the use of a pair of jaws with one jaw being movable within a cavity of the other jaw. A tissue specimen, when removed, would be located within the cavity. Upon removal of the instrument from the tissue taking area and it is desired to remove the tissue from the instrument, the jaws of the instrument are opened and the tissue section within the instrument is automatically moved to the area of the open mouth of the cavity or essentially displaced from the cavity to facilitate removal of the tissue from the instrument. Therefore, there is no need to "dig" the tissue out of the confined volume of the cavity.

DETAILED DESCRIPTION OF THE SHOWN EMBODIMENT

Figure 1:
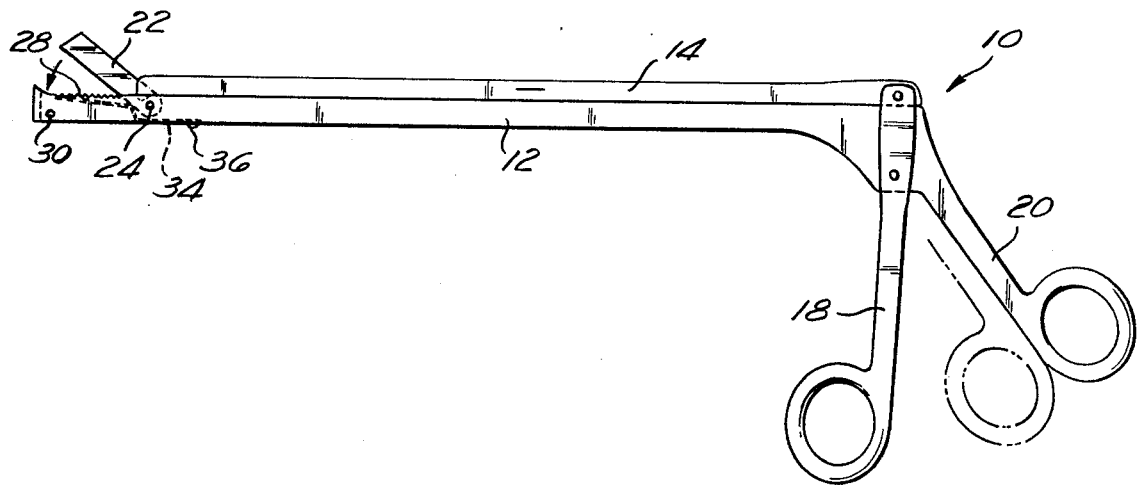
FIG. 1 is a side view of an example of the tissue taking instrument with the jaws of the instrument in the open position and the instrument including the structure of this invention to facilitate the removal of the tissue specimen from the instrument.

Referring particularly to the drawing there is shown an instrument 10 to facilitate the taking of tissue specimens which comprises generally a first elongated member 12 and a second elongated member 14. The members 12 and 14 are interconnected together so as to be movable in respect to each other as through a dove tail slot arrangement 16. The aft end of the member 14 is connected to a first manually graspable member 18 while and aft end of the member 12 also includes a manually graspable member 20. A member 18 is pivotly mounted on both the member 12 and the aft end of the member 14. The member 20 is fixedly secured to the member 12.

The fore end of the member 14 is pivotly attached to a movable member 22. The member 22 is also pivotly secured by means of a pivot pin 24 to the member 12.

The fore end of the member 12 includes a cavity 26 which has an upper edge which defines a cutting edge 28. Mounted within the cavity 26 adjacent the bottom thereof is a pin member 30.

The member 22 is to be movable from the solid line position (open position) shown in the drawings to be locatable within the cavity 26. The size of the member 22 is to closely conform to the interior wall of the cavity 26. Therefore, it can be readily seen that with a section of tissue located between the member 22 and the cutting edge 28, that upon moving of the member 22 to within the cavity 26, that section of tissue will be removed by being cut by the cutting edge 28 and then located within the cavity 26.

After the instrument has been removed from the tissue taking area, it is necessary to remove the section of the tissue from the instrument. The member 22 is first moved to the open position. It is to be understood that the movement of the member 22 into and out of the cavity 26 is accomplished by manually moving together apart the manually graspable sections 18 and 20. The tissue located within the cavity 26 is in contact with a thin metallic plate 32 which is located within the cavity 26. Prior to the opening of the member 22, the plate 32 will probably be in contact with the pin 30 which functions as a stop for the lower position of the plate 32. The plate 32 is integrally connected to a rear section 34 which is mounted flush to an exterior surface of the member 12. This rear section 34 is fixedly secured at its outer end thereof to the elongated member 12 by means of a rivet 36.

Figure 2:
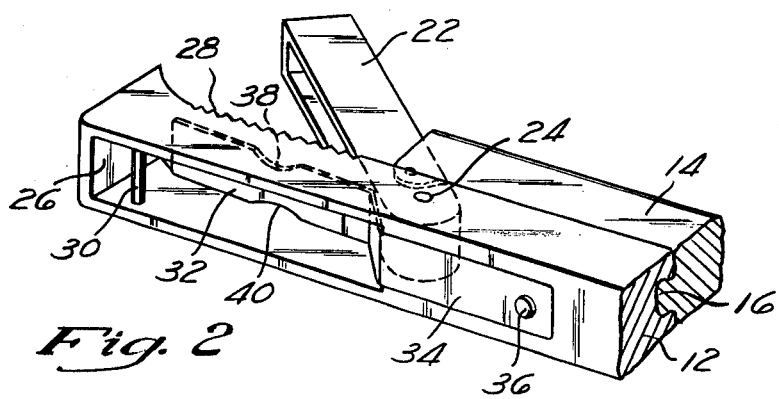
FIG. 2 is an enlarged isometric view of the jaw portion of the instrument of FIG. 1 showing more clearly the structure of this invention to facilitate the removal of a tissue specimen from the instrument.
Figure 3:
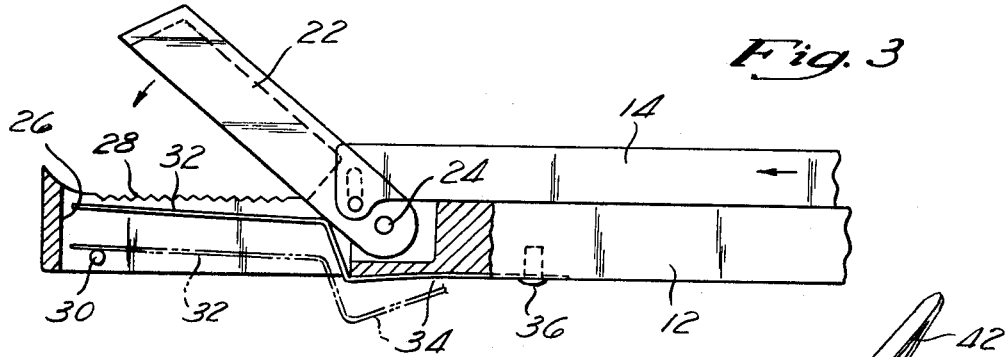
FIG. 3 is a partly cross sectional side view of the jaw portion of the instrument of this invention showing the movable member within the cavity to facilitate removal of the tissue specimen from the instrument.
Figure 4:
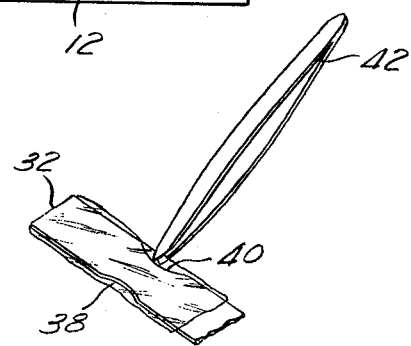
FIG. 4 is an isometric view of the member located within the cavity of the instrument of this invention showing its interelationship with a tweezers to facilitate the removal of the section of tissue from the member.

Upon the opening of the jaw 22, the member 32 will be automatically moved to the solid line position shown in FIGS. 2 and 3 of the drawing which locates member 32 directly adjacent the cutting edge 28. This is accomplished by reason of the inherent "springyness" of the combined members 32 and 34 so that such functions as a leaf spring. As a result, the members 32 and 34 have a continuous bias tending to locate the member 32 in the at rest position adjacent the cutting edge 28.

Therefore, the tissue which has been removed and is now located upon the plate 32, upon removing of the member 22 from the cavity 26, that tissue will be automatically moved outwardly from the cavity 26 to be located directly adjacent the cutting edge 28. Essentially, the tissue has now been displaced from the cavity 26 and therefore subsequent removal of the tissue from the plate 32 is readily facilitated. The removal of the tissue from the plate 32 can be further facilitated by the plate 32 being relieved by cut-out sections 38 and 40 formed on the plate 32. The cut-out sections 38 and 40 are to facilitate the insertion of an instrument such as a pair of tweezers 42 to grasp the tissue which is now supported upon the plate 32.

It is to be understood that although the structure of this invention has been described in relation to a single type of tissue taking instrument, it is to be considered to be in the scope of this invention that a similar type of tissue ejection structure could be included within any other type of tissue taking instrument.

What is claimed is:

1. An instrument for taking tissue specimens comprising:
    a first elongated member having a first fore end and a first aft end;
    a second elongated member having a second fore and and a second aft end, said first and second elongated members being connected together and movable in relation to each other, said aft ends cooperating to form a manually graspable section for causing relative movement of said first and second elongated members;
    said first fore end including a cavity, said cavity being formed by a sidewall, said sidewall having an outer edge, said outer edge including a cutting blade, said second fore end including a third member movable into and out of said cavity, means located within said cavity, said means being movable within said cavity between a lower position and an upper position, said lower position establishing the maximum size of said cavity, said upper position establishing the minimal size of said cavity, whereby a tissue specimen is to be forced into said cavity by moving of said third member into said cavity causing the tissue specimen to be served by said cutting blade, and upon removing of said third member from said cavity said means moves to said upper position and causes the tissue specimen to be substantially displaced from said cavity; and
    said means including relief means for facilitating cooperation with a pair of tweezers to remove said tissue specimen located on said means.

2. The instrument as defined in claim 1 wherein: said means being continuously biased tending to locate such in said upper position.

3. The instrument as defined in claim 2 wherein: said means comprising a thin metallic plate functioning as a leaf spring.

4. The instrument as defined in claim 3 wherein: said leaf spring being attached to said second member, stop means located within said cavity upon said thin plate contacting said stop means said thin plate is located within said lower position.

5. The instrument as defined in claim 4 wherein:
    said relief means comprising cut-out sections on each side thereof.

* * * * *